United States Patent [19]
Heaton et al.

[11] Patent Number: 5,901,895
[45] Date of Patent: May 11, 1999

[54] ARTICULATING APPARATUS FOR APPLYING SURGICAL FASTENERS TO BODY TISSUE

[75] Inventors: Lisa W. Heaton, Norwalk; Mitchell J. Palmer, New Milford; Keith L. Milliman, Bethel, all of Conn.; Richard C. McClure, Claremont, Calif.; Alan B. Bachman, Hamden, Conn.

[73] Assignee: United States Surgical Corporation, Norwalk, Conn.

[21] Appl. No.: 08/726,029

[22] Filed: Oct. 4, 1996

Related U.S. Application Data

[63] Continuation-in-part of application No. 08/318,593, Oct. 5, 1994, abandoned.

[51] Int. Cl.$^6$ .................................................. A61B 17/068
[52] U.S. Cl. ...................... 227/176.1; 227/19; 227/178.1
[58] Field of Search .............................. 227/175.1, 176.1, 227/178.1, 179.1, 19

[56] References Cited

U.S. PATENT DOCUMENTS

| | | |
|---|---|---|
| 3,079,606 | 3/1963 | Bobrov . |
| 3,490,675 | 1/1970 | Green et al. . |
| 3,499,591 | 3/1970 | Green . |
| 3,892,228 | 7/1975 | Mitsui . |
| 4,207,873 | 6/1980 | Kruy . |
| 4,688,555 | 8/1987 | Wardle . |
| 4,728,020 | 3/1988 | Green et al. . |
| 4,880,015 | 11/1989 | Nierman . |
| 4,938,408 | 7/1990 | Bedi et al. . |
| 5,018,657 | 5/1991 | Pedlick et al. . |
| 5,040,715 | 8/1991 | Green et al. . |
| 5,271,543 | 12/1993 | Grant et al. . |
| 5,312,023 | 5/1994 | Green et al. . |
| 5,318,221 | 6/1994 | Green et al. . |
| 5,326,013 | 7/1994 | Green et al. . |
| 5,348,259 | 9/1994 | Blanco et al. . |
| 5,356,064 | 10/1994 | Green et al. ............................... 227/19 |
| 5,431,323 | 7/1995 | Smith et al. . |
| 5,485,952 | 1/1996 | Fontayne . |
| 5,547,117 | 8/1996 | Hamblin et al. .......................... 227/19 |

FOREIGN PATENT DOCUMENTS 0324637  7/1989  European Pat. Off. .

*Primary Examiner*—Scott A. Smith

[57] ABSTRACT

Apparatus for applying surgical fasteners to body tissue which includes a body having a proximal portion defining a central longitudinal axis and an articulating distal portion; a fastener cartridge containing at least one surgical fastener therein and positionable in the articulating distal portion; an anvil mounted adjacent the fastener cartridge and defining a fastener forming surface against which surgical fasteners are formed when ejected from the fastener cartridge; a fastener driving mechanism operatively associated with the fastener cartridge and actuatable from the handle to eject the at least one fastener from the fastener cartridge; a link member having a distal portion offset from the body central longitudinal axis and pivotably connected to the articulating distal portion at a point spaced from the body central longitudinal axis, the link member being movable between a proximal-most position to move the distal portion to an articulated condition away from the central longitudinal axis on a first side of the body and a distal-most position to move the distal portion to an articulated condition away from the central longitudinal axis on a second side of the body; and a control lever connected to the link member and pivotable about a point located along the body central longitudinal axis between a first position corresponding to the proximal-most position of the link member and a second position corresponding to the distal-most position of the link member.

7 Claims, 12 Drawing Sheets

ARTICULATING APPARATUS FOR APPLYING SURGICAL FASTENERS TO BODY TISSUE

CROSS-REFERENCE TO RELATED APPLICATIONS

The present application is a continuation-in-part of commonly assigned, co-pending U.S. application Ser. No. 08/318,593, filed on Oct. 5, 1994, now abandoned, by Heaton et al.

BACKGROUND

1. Technical Field

The technical field relates to a surgical apparatus, and more particularly to a surgical stapling apparatus that can perform operations such as articulation, tissue clamping, staple forming and/or tissue cutting.

2. Background of Related Art

Surgical stapling instruments are known wherein tissue is first grasped or clamped between opposing jaw structure and then fastened by means of fasteners. In some instruments a knife is provided to cut tissue which has been joined by the fasteners. The fasteners are typically in the form of surgical staples, however, two part polymeric type fasteners are also known.

Instruments for this purpose can include two elongated jaws which are respectively used to capture or clamp tissue. Typically, one of the jaws carries a disposable cartridge wherein a plurality of staples are arranged in at least two lateral rows while the other jaw has an anvil for forming the staple legs as the staples are driven from the cartridge. Generally, the stapling operation is effected by a camming element which travels longitudinally through the cartridge carrying member and acts upon individual staple pushers to sequentially eject the staples from the cartridge. A knife can be positioned in such a manner so as to operate sequentially immediately behind the camming element and laterally positioned between the staple rows to longitudinally cut and/or open the stapled tissue between the rows of staples. Such instruments are disclosed in Bobrov et al. (U.S. Pat. No. 3,079,606) and Green '675 (U.S. Pat. No. 3,490,675).

A later instrument disclosed in U.S. Pat. No. 3,499,591 to Green applies a double row of staples on each side of the incision. This is accomplished by a cartridge assembly wherein a cam member moves within an elongate guide path between two sets of staggered staple carrying grooves. Staple drive members are positioned in such a manner so as to be contacted by the longitudinally moving cam to effect ejection of the staples. The cartridge assemblies typically come in a plurality of sizes, each varying in both length and number of staples contained therein. Depending on the procedure to be performed, the surgeon must select the appropriate cartridge assembly.

The instruments described above were all designed for use in surgical procedures wherein surgeons have direct access to the operation site. However, in endoscopic or laparoscopic procedures, surgery is performed through a small incision or through narrow cannulae inserted through entrance wounds in the skin. In order to address the specific needs of endoscopic and/or laparoscopic surgical procedures, endoscopic surgical stapling devices such as those disclosed in U.S. Pat. No. B5,040,715 and U.S. Pat. No. 5,318,221, both to Green et al., have been developed. In general, these instruments are provided with clamping structure to effect approximation of an anvil and a staple cartridge to secure tissue therebetween, and staple firing structure to effect sequential ejection of a plurality of staples from the staple cartridge after the tissue has been secured.

Many of the instruments described above are limited in their range of operability. Improvements, however, have been made in the art of surgical instruments to provide increased range of operability. For example, U.S. Patent Nos. 5,312,023 and 5,326,013, both to Green et al., are directed to a surgical apparatus having a mechanism for effectuating the articulation of a fastener applying assembly disposed at a distal end of the instrument. The mechanism to effectuate articulation includes a rotatable dial member operatively associated with the exterior of the elongated tubular section and is connected to a cable loop or linkage which effects articulation. By turning the dial, the fastener applying assembly at the distal end of the instrument can be caused to articulate, i.e., bend away from the longitudinal axis of the instrument.

While the dial concept is useful, it would be helpful to provide the surgeon with an external articulation actuator mechanism that is movable in a manner that externally indicates the state of articulation of the fastening and cutting portion of the instrument relative to the elongated tubular shaft of the instrument. In laparoscopic procedures, such a mechanism would permit the surgeon to know the state of articulation without having to check video monitors. It would also be beneficial to provide an instrument including an actuation control member which is more readily and conveniently accessible to the user and which is easier to control during surgical procedures.

SUMMARY

An apparatus is provided for applying a plurality of surgical fasteners to body tissue which includes a handle assembly and an elongated body extending from the handle assembly and defining a longitudinal axis. A cartridge housing is also provided and is pivotably connected to a distal end portion of the elongated body. The cartridge housing is configured to receive a fastener cartridge containing a plurality of surgical fasteners therein. The apparatus also includes an anvil mounted adjacent the cartridge housing and defining a fastener forming surface against which surgical fasteners are driven when ejected from the fastener cartridge. A fastener driving mechanism is provided in operative association with the fastener cartridge and is actuatable from the handle assembly to eject fasteners from the fastener cartridge.

A linkage mechanism is operatively associated with the cartridge housing to pivotably move the cartridge housing between a first position in alignment with the longitudinal axis of the elongated body, and a second position out of alignment with the longitudinal axis. A control lever, which provides external visual indication to the user of the relative position of the cartridge housing with respect to the elongated body, is operatively connected to the linkage mechanism and movable between a first position corresponding to the first position of the cartridge housing and a second position corresponding to the second position of the cartridge housing.

Alternative features of the apparatus include the elongated body being rotatably disposed relative to the handle body and a clamping mechanism operatively associated with the anvil to move the anvil relative to the cartridge housing and to clamp tissue therebetween. In one preferred embodiment, the clamping mechanism includes a plurality of elongated flexible bands which flex upon movement of the cartridge housing from the first position to the second position. The flexible bands permit clamping while the instrument is articulated or in the second position. The clamping mechanism can further include a cam operatively associated with the anvil and the plurality of elongated bands.

The fastener driving mechanism also preferably includes a plurality of elongated flexible bands which flex upon movement of the cartridge housing from the first position to the second position. The flexible bands permit firing while the instrument is articulated or in the second position. A camming member may be included in the fastening firing mechanism, which is adapted to urge the fasteners from the fastener cartridge. Preferably the camming member moves in a distal direction to urge the fasteners from the fastener cartridge.

The clamping mechanism of an alternative configuration of the apparatus is actuable from the handle assembly to move the anvil relative to the cartridge housing to clamp tissue therebetween and includes a first link, a reversing member operatively connected to the first link member and having a distal end, a second link operatively connected to the distal end of the reversing member and a pair of pivotably connected clamp fingers, operatively connected to the reversing member. In this configuration, proximal movement of the first link results in distal movement of the second link.

The present disclosure in an alternative embodiment provides an apparatus for applying surgical fasteners to body tissue which includes a body having a proximal portion defining a central longitudinal axis and an articulating distal portion; a fastener cartridge containing at least one surgical fastener therein and positionable in the articulating distal portion; an anvil mounted adjacent the fastener cartridge and defining a fastener forming surface against which surgical fasteners are formed when ejected from the fastener cartridge; a fastener driving mechanism operatively associated with the fastener cartridge and actuatable from the handle to eject the at least one fastener from the fastener cartridge; a link member having a distal portion offset from the body central longitudinal axis and pivotably connected to the articulating distal portion at a point spaced from the body central longitudinal axis, the link member being movable between a proximal-most position to move the distal portion to an articulated condition away from the central longitudinal axis on a first side of the body and a distal-most position to move the distal portion to an articulated condition away from the central longitudinal axis on a second side of the body; and a control lever connected to the link member and pivotable about a point located along the body central longitudinal axis between a first position corresponding to the proximal-most position of the link member and a second position corresponding to the distal-most position of the link member.

In one aspect of the present disclosure, the control lever defines a pivot point and includes an elongated portion extending from the pivot point, wherein when the control lever is positioned in the first position, the elongated portion is disposed to the first side of the body and when the control lever is positioned in the second position, the elongated portion is disposed to the second side of the body.

In a further aspect of the presently disclosed surgical fastener applying apparatus, the distal portion is moveable to an articulated condition up to 35 degrees from the central longitudinal axis.

In another alternative embodiment, the present disclosure provides an apparatus for applying surgical fasteners to body tissue, which includes a handle; an elongated body extending from the handle and defining a central longitudinal axis; a fastener cartridge housing pivotably connected to a distal end portion of the elongated body; a fastener cartridge containing a plurality of surgical fasteners and positionable in the cartridge housing; an anvil mounted adjacent the cartridge housing and defining a fastener forming surface against which surgical fasteners are driven when ejected from the fastener cartridge; a fastener driving mechanism operatively associated with the fastener cartridge and actuatable from the handle to eject fasteners from the fastener cartridge; a link member having a distal portion offset from the elongated body central longitudinal axis and pivotably connected to the cartridge housing, the link member being movable between a proximal-most position to move the cartridge housing to an articulated condition to a first side of the elongated body central longitudinal axis and a distal-most position to move the cartridge housing to an articulated condition to a second side of the elongated body central longitudinal axis; and a control lever connected to the handle and pivotable about a point located along the elongated body central longitudinal axis connected to the link and pivotable between a first position corresponding to the proximal-most position of the link member and a second position corresponding to the distal-most position of the link member.

In one aspect of the presently disclosed apparatus for applying surgical fasteners the elongated body is rotatably connected to the handle.

BRIEF DESCRIPTION OF THE DRAWINGS

Various embodiments are described herein with reference to the drawings, wherein:

FIGS. 4A and 4B are enlarged partial cross-sectional views, which illustrate the articulation capability of the fastening and cutting portion and the associated control lever positions of the instrument of FIG. 1, respectively;

FIG. 5A is an enlarged, partial cross-sectional view of the distal end of the stapling instrument, which illustrates the reverser link and clamp cam;

DETAILED DESCRIPTION OF PREFERRED EMBODIMENTS

Figure 1:
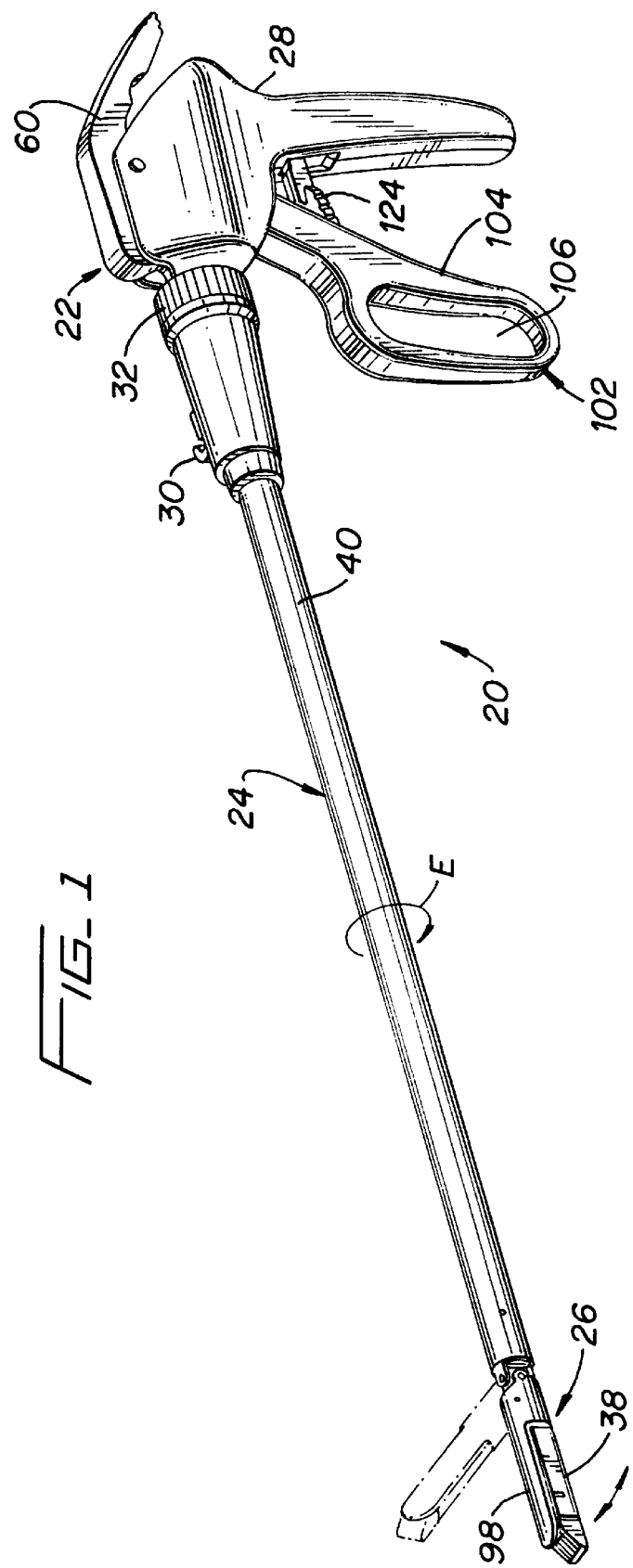
FIG. 1 is a perspective view of a surgical stapling instrument in accordance with the present disclosure.

It is generally accepted that endoscopic procedures are more common than laparoscopic procedures. Accordingly, the following embodiments shall be discussed in terms of endoscopic procedures and apparatus. However, use herein of terms such as "endoscopic", "endoscopically" and "endoscopic portion", among others, should not be construed to limit the claims appended hereto to a stapling and cutting apparatus for use only in conjunction with an endoscopic tube. On the contrary, it is believed that the embodiments described herein may find use in any procedure where access is limited to a small incision, including but not limited to laparoscopic procedures. Also, as used herein the terms "fasteners" and "staples" shall be treated equivalently. Unless otherwise stated, the term "cartridge assembly" shall include at least the cartridge itself and staples or fasteners and staple drive members disposed therein. In the drawings and the description which follows, as is customary, the term "proximal" refers to the end which is closest to the operator when the instrument is in use, while the term "distal" will refer to the end which is furthest from the operator during use thereof.

Preferred embodiments of the surgical stapler will now be described in detail with reference to the drawings, wherein like reference numerals designate identical or corresponding parts throughout the several views. In FIG. 1, a surgical stapler is illustrated and designated generally by reference numeral 20. Surgical stapler 20, as noted above, is configured to engage body tissue, apply a plurality of surgical fasteners thereto, and form an incision in the fastened body tissue during an endoscopic surgical procedure. In brief, surgical stapler 20 includes a handle portion 22, an elongate body portion 24 extending distally from handle portion 22, and a fastening and cutting portion 26 operatively associated with a distal end of body portion 24.

Figure 2:
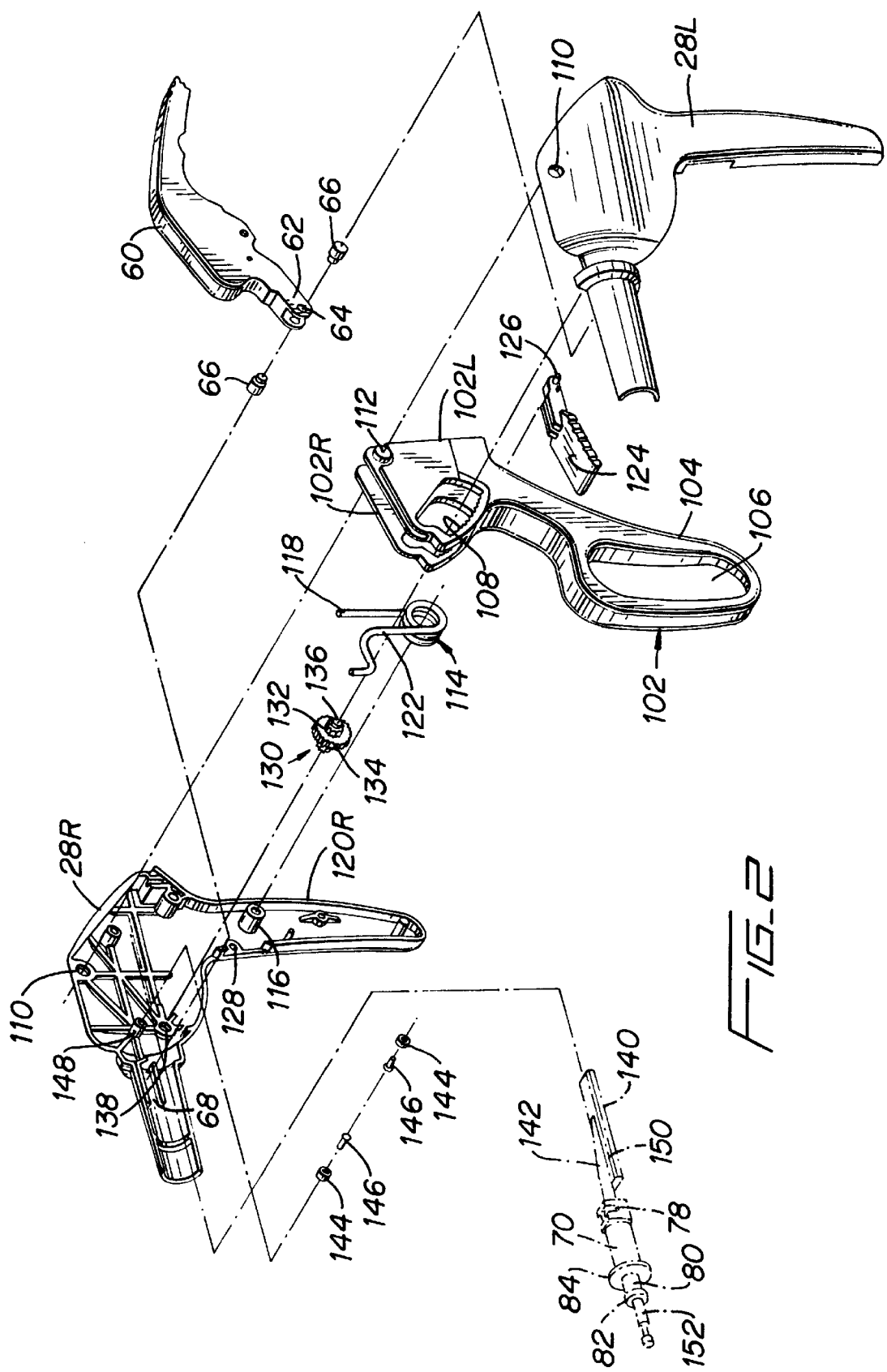
FIG. 2 is a perspective view, with parts separated, of the handle assembly of the instrument of FIG. 1.

Referring to FIG. 2, the handle portion 22 of surgical apparatus 20 is shown and includes a handle body 28 that has two parts, a left body portion 28L and a right body portion 28R. These portions are optimally fastened together by means of ultrasonic welding along the peripheral contacting surfaces thereof, although screws, adhesives, press fit structures or other suitable means of joining the two handle body parts may also be utilized. The handle body 28 is of an overall size and shape convenient for being held in one hand.

The structural elements providing for articulation of fastening and cutting portion 26 and rotation of elongate body portion 24 will now be described with reference to FIG. 2–4B. Articulation control lever 30 is pivotally mounted to rotation handle 32 such that articulation control lever 30 pivots about pin 34, as shown in FIG. 4B. Actuation control link rod 36 has longitudinal slot 36b and transverse slot 36a. In the unarticulated position, external elongate section 30a of lever 30 is generally parallel with axis "C" of the instrument, as is the axis "C"" of fastening assembly 26. To articulate fastener assembly 26 away from axis "C", lever 30 is pivoted about pin 34. This pivoting action causes pin 35' to slide in transverse slot 36a of rod 36 and further causes rod 36 to move proximally, thereby articulating fastener assembly 26. Slot 36b permits rod 36 to move longitudinally relative to pin 34.

Cartridge housing 38 is pivotally mounted to tube cover 40 by rivet 42 at extended finger portion 44 such that rivet 42 passes through a centrally disposed bore formed through the proximal end of cartridge housing 38. Cartridge housing 38 is pivotally attached at a bore formed therein which is adjacent to the bore which receives rivet 42 to a distal end portion of articulation control link rod 36. In this manner, reciprocal longitudinal motion of articulation control link rod 36 pivots cartridge housing 38 about rivet 42 such that fastening and cutting portion 26 articulates to one side of surgical instrument 20 toward and away from a central longitudinal axis "C" thereof. One preferred configuration for such articulation has provided for a radius of motion angle of approximately 30° to 35° as measured from the central longitudinal axis "C" of surgical stapler 20.

Additional structural elements are provided to support fastening and cutting portion 26. In particular, a pivot post 46 is mounted near the distal end of cover tube 40, for example, by a pin 48 passing through transverse bores formed in legs 50 extending proximally from pivot post 46 (shown in FIG. 4A). Pivot post 46 preferably includes a shield 52 formed on one side thereof and extending distally therefrom. Shield 52 prevents the creation of a pinch point wherein tissue may become trapped when surgical stapler 52 is moved from the articulated position to the longitudinal aligned position. Also provided are a lower pivot 54, a pivot plate 56 and a support 58 each of which add stability to the pivotally mounted fastening and cutting portion 26.

Rotation handle 32 is an abbreviated frustoconical structure having a central bore formed by the joining of arcuate split sections 32a and 32b. The split sections are preferably ultrasonically welded along the peripheral contacting surfaces thereof, although screws, adhesives, press fit structures or other suitable means of joining the two parts may also be utilized. A pair of longitudinally spaced extended tabs 33 are positioned on an interior facing arcuate collar portion at the distal ends of each of split sections 32a and 32b and engage correspondingly spaced indentations 35 formed oppositely on the exterior surface of cover tube 40. At a proximal end of rotation handle 32, knurling 37 may be provided to facilitate rotation. Because of the engaging structural relationship of the rotation handle 32 and cover tube 40, rotation of handle 32 effects rotation of cover tube 40, indicated by Arrow "E" in FIG. 1 and, therefore, rotation of the articulated fastening and cutting portion 26, as shown in phantom lines also in FIG. 1.

The structural components of the clamp subassembly of surgical stapler 20 will now be described with continued reference to FIGS. 1–3. A clamp approximation control lever 60 is pivotally mounted within handle body 28 for movement between an open position and a closed position. At a distal end, the clamp lever 60 is provided with a fork portion 62 having a pair of transversely aligned apertures 64 for receiving clamp lever pins 66. Pins 66 pass through apertures 64 and interfit in slots 68 formed on the inside wall of body portions 28L and 28R for longitudinal reciprocal movement therein.

A pusher member 70 is provided to interconnect the clamp approximation control lever 60 and a clamp pusher tube 72, such that an elongated bore 74, formed longitudinally through pusher member 70, is in communication with the hollow interior 76 (FIG. 6) of clamp pusher tube 72. A pair of U-shaped indented surfaces 78 are formed near a distal end of pusher member 70 and are sized to loosely receive pins 66 for fee rotation of same.

Pusher member 70 has a longitudinally, distally extending reduced diameter end portion 80 with a plug 82 formed at a distal end thereof. End portion 80 is inserted into the open proximal end of clamp pusher tube 72. Pusher member 70 has a flange 84 which is secured to the proximal end of clamp pusher tube 72 by, for example, welding, bonding or other suitable known techniques. In this manner, reciprocal longitudinal motion of clamp pusher tube 72 is induced by raising and lowering clamp approximation control lever 60. Alternatively, plug 82 may be of such diameter as to provide for a friction fit within the interior wall of clamp pusher tube 72.

A clamp link 86 is interconnected with clamp pusher tube 72 by a pin 88 inserted through a transverse bore formed at the distal end of clamp pusher tube 72 and passing through longitudinal slot 90 (shown in FIG. 5A). Slot 90 allows pusher tube 72 to travel a predetermined distance before causing movement of clamp link 86, as will be described in detail below.

A reverser link 92 is pivotally mounted to tube cover 40 by pin 48, interfitted between legs 50 of pivot post 46 (as shown in FIG. 4A). Reverser link 92 pivots about a point on surgical stapler 20 which is fixed relative to handle body 28. Reverser link 92 is further pivotally connected at one end to a distally extending portion of link 86 and at the other end to laterally stacked flexible clamp links 94. Flexible clamp links 94 are preferably thin bands formed of a resilient flexible material, such as stainless steel or other similar materials, which exhibit similar flexibility and strength characteristics. Upon articulation of fastener and cutting portion 26, flexible pushers 166 and flexible clamp lengths 94 bend to allow for such articulation. In this manner, distal movement of clamp pusher tube 72 is translated by pivoting of reverser link 92 to proximal movement of flexible clamp links 94. Distal end portions of clamp links 94 are pivotally connected to clamp cam 96, which in turn is pivotally interconnected to anvil 98. The motion of clamp cam 96 is governed by caming pin 100 passing through can slot 101 (FIG. 5A) which is frictionally fitted in a bore formed transversely through cartridge housing 38. Thus, reciprocating motion of clamp pusher tube 72 translates to clamping motion of anvil 98.

Figure 3:
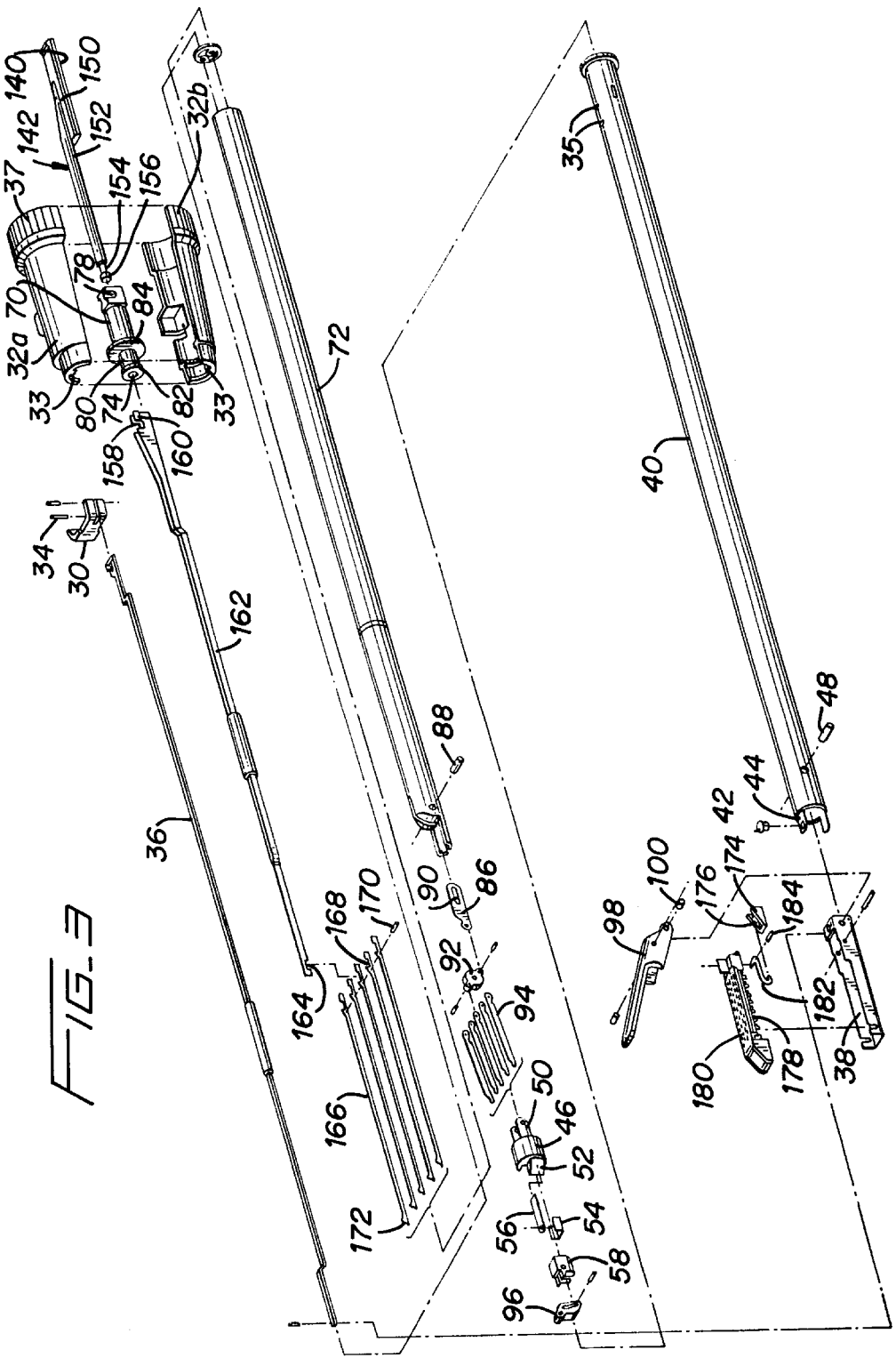
FIG. 3 is a perspective view, with parts separated, of the interior structural components of the various operational features of the instrument of FIG. 1.
Figure 4:
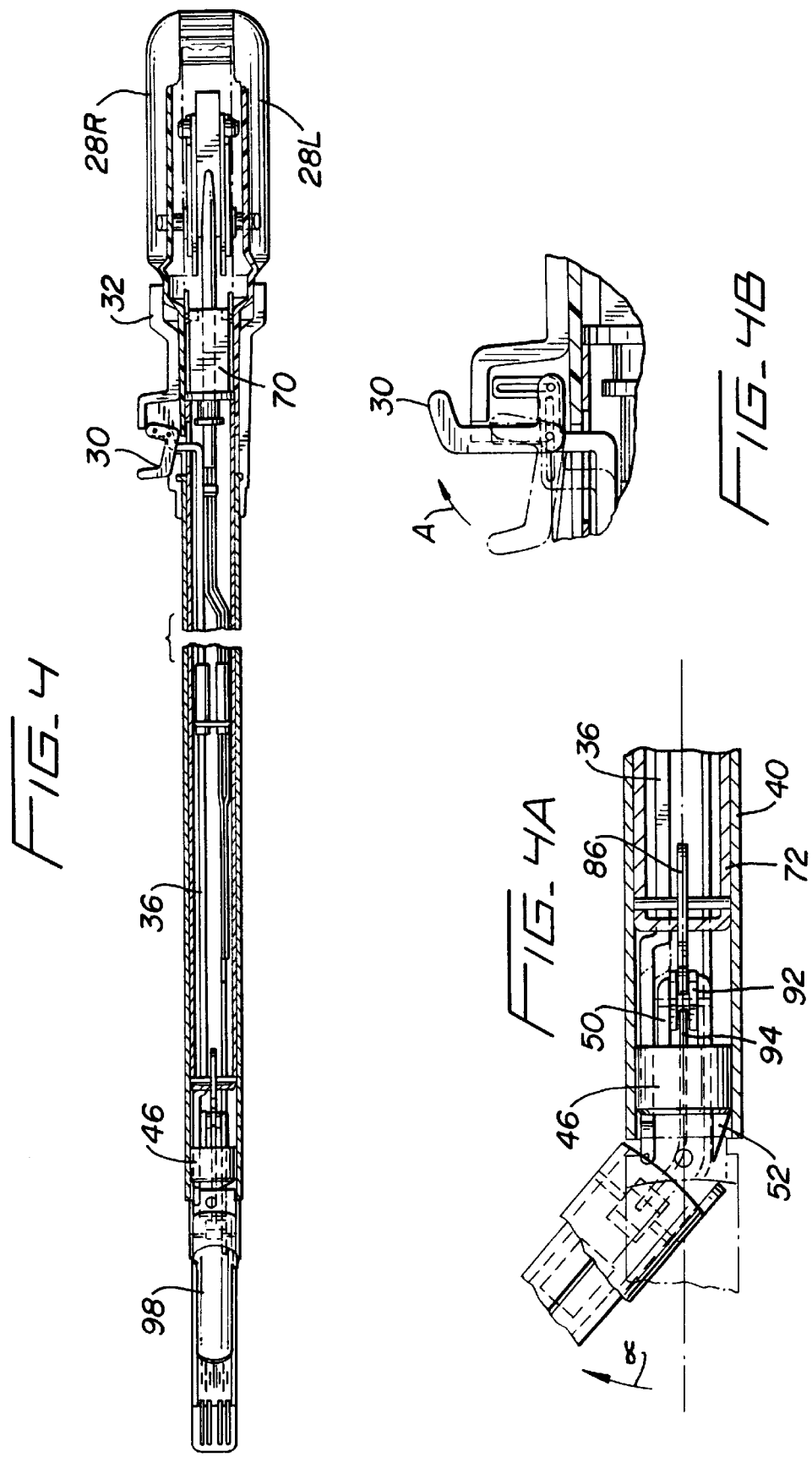
FIG. 4 is a top cross-sectional view which illustrates the articulation control structural components of the instrument of FIG. 1.

Referring to FIGS. 1–3, a trigger 102 has a shank portion 104 which forms an opening 106 sized to enable the user to grasp shank 104 by inserting a plurality of fingers therein and to facilitate squeezing it in a trigger like fashion. Trigger 102 includes web portions 102L and 102R extending from shank portion 104. Each of web portions 102L and 102R include an aperture formed therein such that, on one internal surface of the aperture, an arcuate rack 108 is formed. Transverse apertures 110 are formed in frame portions 28L and 28R to receive raised pin portions 112 which extend transversely from the upper portion of each of trigger webs 102L and 102R. Thus, trigger 102 pivots within handle body 28 about transverse apertures 110. A coil spring 114 is mounted within body portions 28L and 28R on a transversely extending boss 116 formed on the inside wall of handle body portion 28R. Spring leg 118 biases firmly against a rear wall (FIGS. 5 and 6) of handle body 28, formed by portions 120L and 120R of body portions 28L and 28R, respectively. Spring leg 122 biases trigger 102 away from handle body 28 toward a prefired position (also shown in FIGS. 5 and 6).

With continued reference to FIGS. 1 and 2, a manual safety 124 is provided to lock trigger 102 in the unfired position to prevent accidental retraction thereof. Safety 124 has transverse projections 126 formed on a proximal end thereof, which interfit into receiving holes 128 formed in handle body portions 28L and 28R for pivotal movement of the safety 124 between an engaged position and a disengaged position. In the engaged position, the distal surface of safety 124 frictionally interfits with a receiving surface (shown in phantom lines in FIGS. 5 and 6) formed on the distal surface of trigger 102. To unlock the trigger 102, safety 124 is simply pivoted downward out of engagement with the receiving surface of trigger 102.

A pinion-spur-gear assembly 130, which includes a pinion gear 132 interfitting with a spur gear 134, provides plural driving surfaces, the unction of which will be described in detail below. Pinion gear 132 is further provided with projections 136 formed at either end thereof which interfit with holes 138 formed in handle body portions 28L and 28R to facilitate rotational motion of pinion-spur-gear assembly 124 about a transverse axis formed by projections 136.

Figure 7:
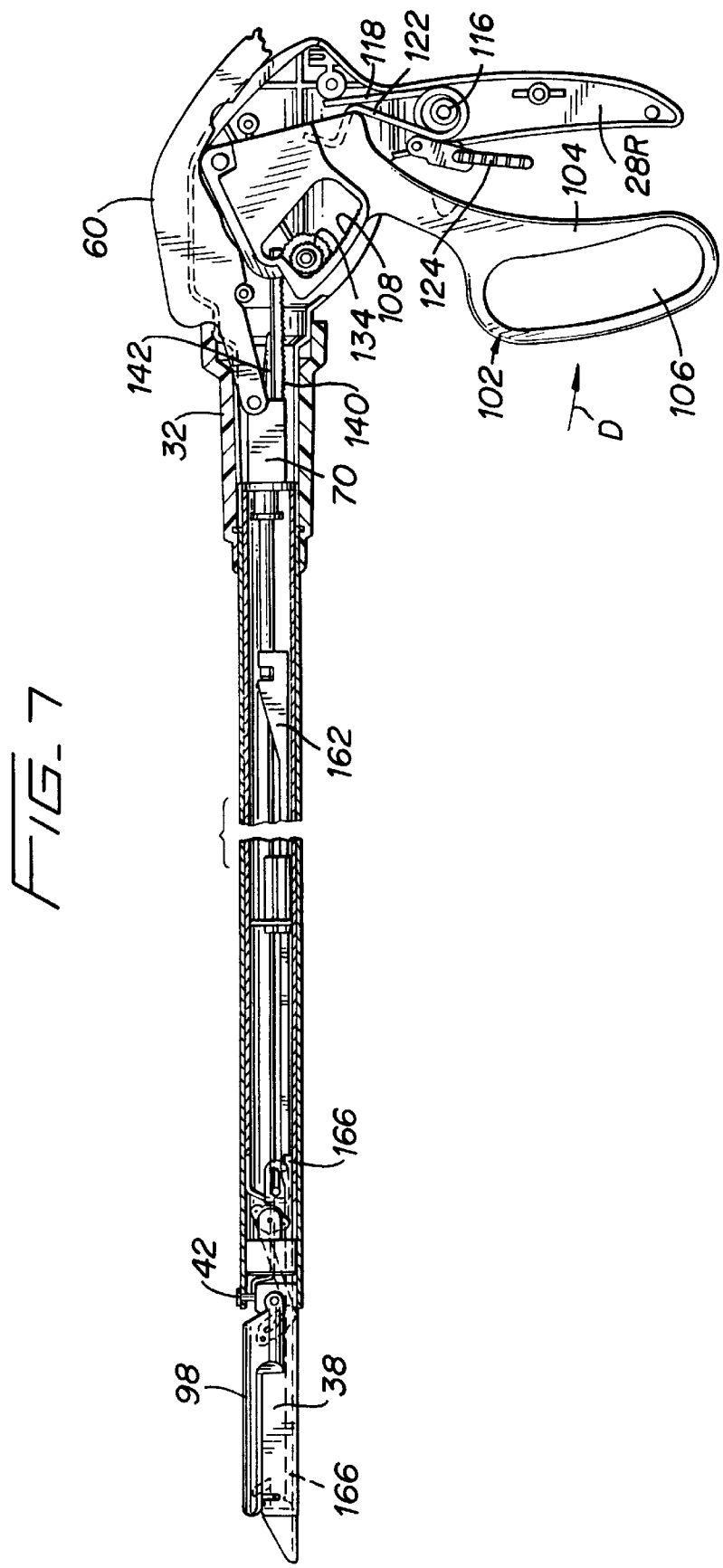
FIG. 7 is a side cross-sectional view, which illustrates actuation of the fastener firing mechanism.
Figure 8:
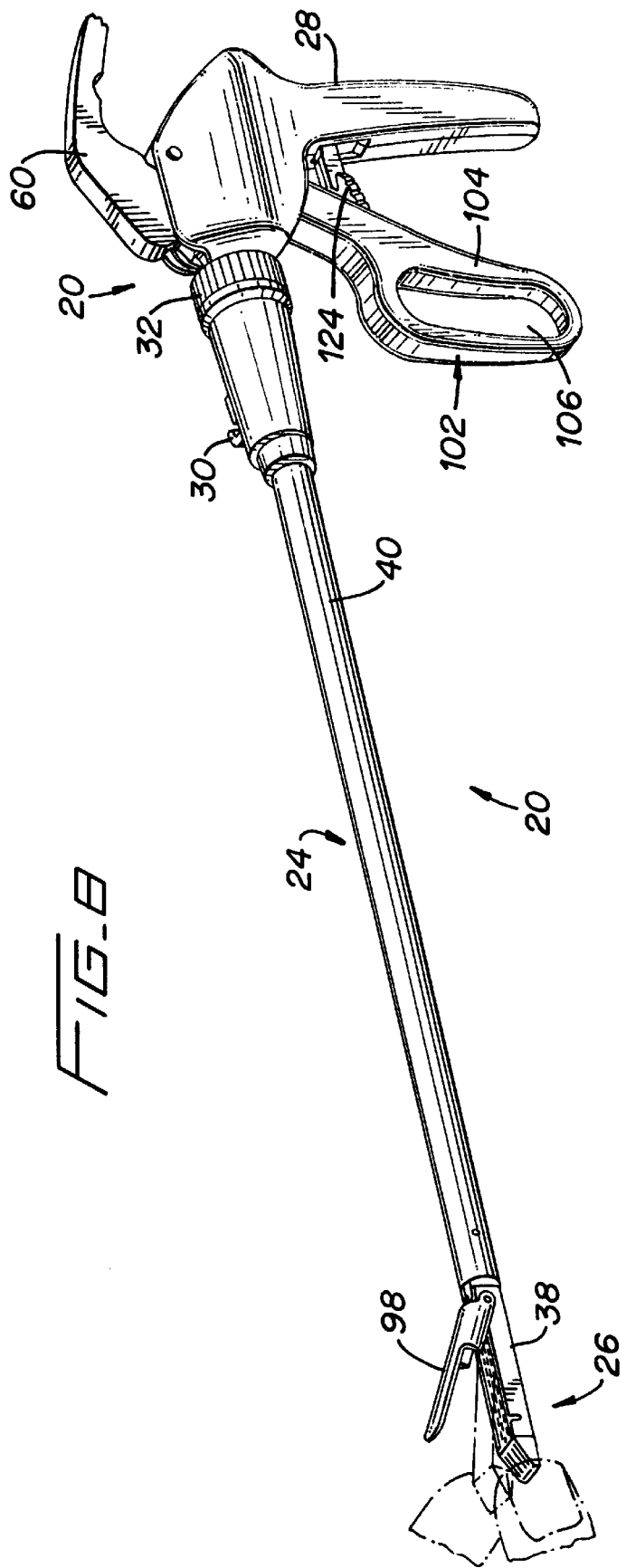
FIG. 8 is a side cross-sectional view, which illustrates replacement of the fastener cartridge.

The driving surface formed by pinion gear 132 engages arcuate racks 108 such that reciprocal motion of trigger 102 rotates the pinion-spur-gear assembly 130 in both clockwise and counterclockwise directions. The driving surface formed by spur gear 134 engages a horizontal longitudinal rack 140 formed in the underside of rack rod 142 (as shown in FIG. 7). Rotation of spur gear 134 translates through the horizontal longitudinal rack 140, to longitudinal reciprocal motion of the rack rod 142.

With continued reference to FIG. 2, in conjunction with FIG. 3, rack rod 142 is longitudinally slidable within handle body 28 atop spur gear 134. A pair of rollers 144 are rotatably fixed relative to handle body portions 28L and 28R by pins 146 engaged in holes 148 formed on the interior of the handle body portions. Rollers 144 abut longitudinal shoulders 150 of rack rod 142 to prevent rack rod 81 from disengaging spur gear 134.

Rack rod 142 is provided with a longitudinal cylindrical shaft 152 having an axially mounted protruding stem 154 and bearing a push plug 156. Push plug 156 preferably has a chamfered distal tip and is configured and dimensioned to be received within a pair of transverse slots 158 formed distally of fingers 160 on a channel 162. Channel 162 is an elongated member having a substantially U-shaped cross-section and is slidably mounted within elongate body portion 24 for reciprocal longitudinal motion therein. Near a distal end of channel 162, a slot 164 is formed which is configured and dimensioned to interfit and engage a proximal end of flexible pusher members 166 at corresponding slots 168 formed therein. Pusher members 166 are preferably formed of a flexible resilient material, such as stainless steel, and are formed as thin bands to provide flexibility for articulation and strength for transmitting force. Flexible pusher members 166 are positioned adjacent one another and fastened together near proximal ends thereof, for example, by a pin 170 passing through transverse holes formed distally of slots 168. Each flexible pusher member 166 is provided with a raised bearing surface 172 formed at a distal end thereof, which bias against a proximal end of a camming sled 174. Sled 174 is preferably formed in a wedge shape and has side walls 176 forming camming surfaces which, as will be described in greater detail below, cam a plurality of individual staple pushers 178 slidably mounted in a replaceable staple cartridge 180 to eject staples therefrom.

A substantially S-shaped knife shank 182 is longitudinally oriented and has a distal hook portion to engage a transverse mounting surface formed on sled 174 to be pulled distally along therewith. A knife blade 184 is mounted on a proximal hook portion of knife shank 182 by any suitable known mounting techniques. Knife blade 184 follows camming sled 174 longitudinally along the length of staple cartridge 180 and between the newly formed rows of staples, as will be described in greater detail below.

The operation of the various subassembly features of surgical stapler 20 will now be described with reference to FIGS. 4A–8. With initial reference to FIG. 4A and 4B, the articulating feature of fastening and cutting portion (or "fastener assembly") 26 is shown. In an initial or unarticulated condition (shown in phantom), articulation control lever 30 is positioned in a distal most orientation corresponding to fastening and cutting portion 26 being substantially aligned with the central longitudinal axis surgical stapler 20. In this position exterior elongate section 30a of control lever 30 is generally aligned with the longitudinal axis of the instrument and the distal fastening assembly. In order to articulate the fastening and cutting portion 26 as shown in FIG. 4A, the user moves articulation control lever 30 proximally in the direction of Arrow "A" shown in FIG. 4B, such that articulation control lever 30 is moved outwardly away from rotation handle 32. Proximal movement of control lever 30 causes the lever to pivot about pin 34 and further causes pin 35' to move in slot 36a of link rod 36. This movement results in proximal movement of link rod 36 and causes the fastener assembly 26 to pivot about rivet 42. In the articulated position, axis "C'" of the fastener assembly is articulated at an angle Ø with respect to axis "C", and section 30a of lever 30 is oriented away from axis "C", thereby indicating articulation.

Therefore, by moving lever 30, the user is provided with a visual indication of the relative orientation of fastening and cutting portion 26 with respect to the longitudinal axis of the instrument.

Figure 5:
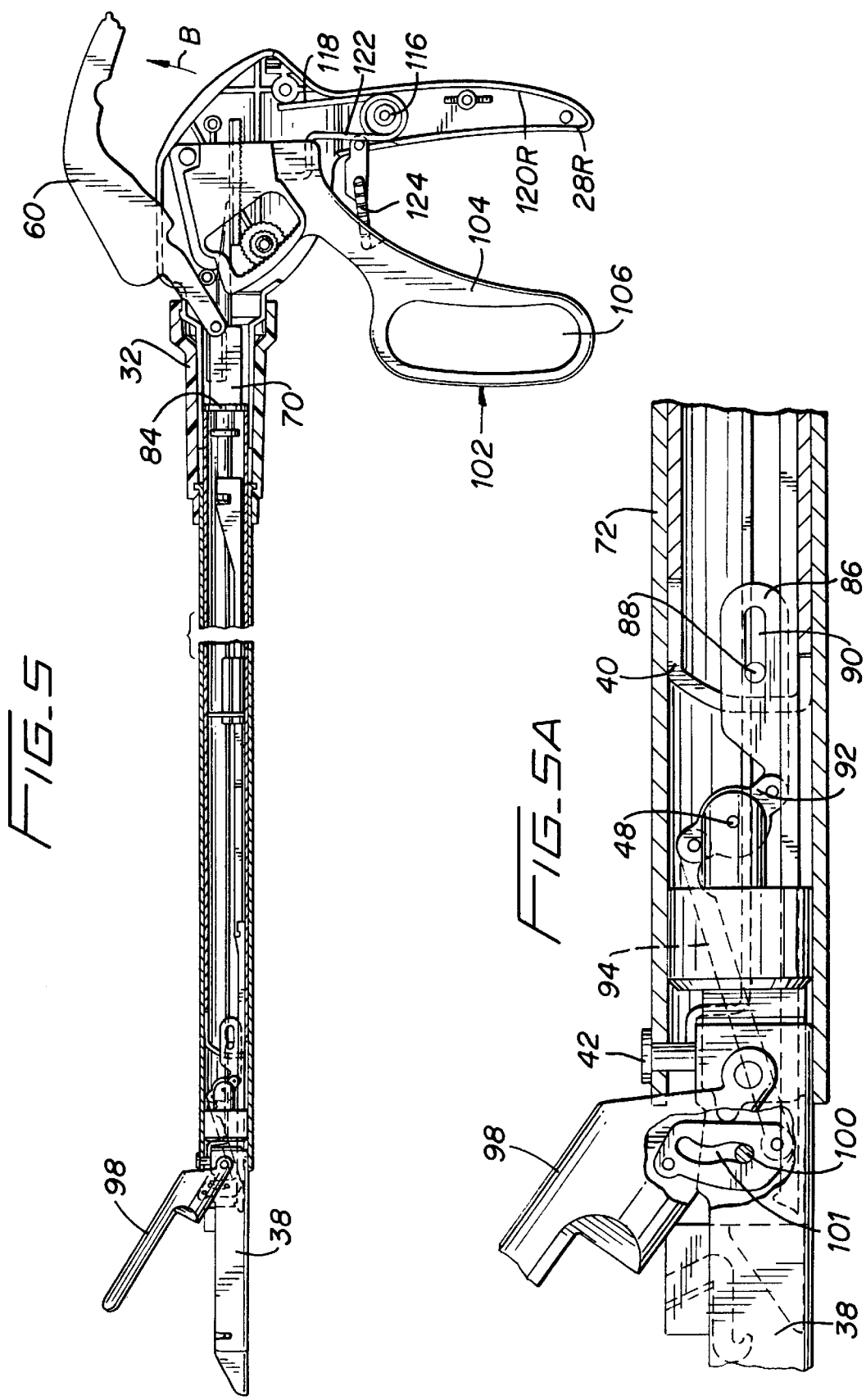
FIG. 5 is a side cross-sectional view, which illustrates the various components of the clamp actuation structure.
Figure 6:
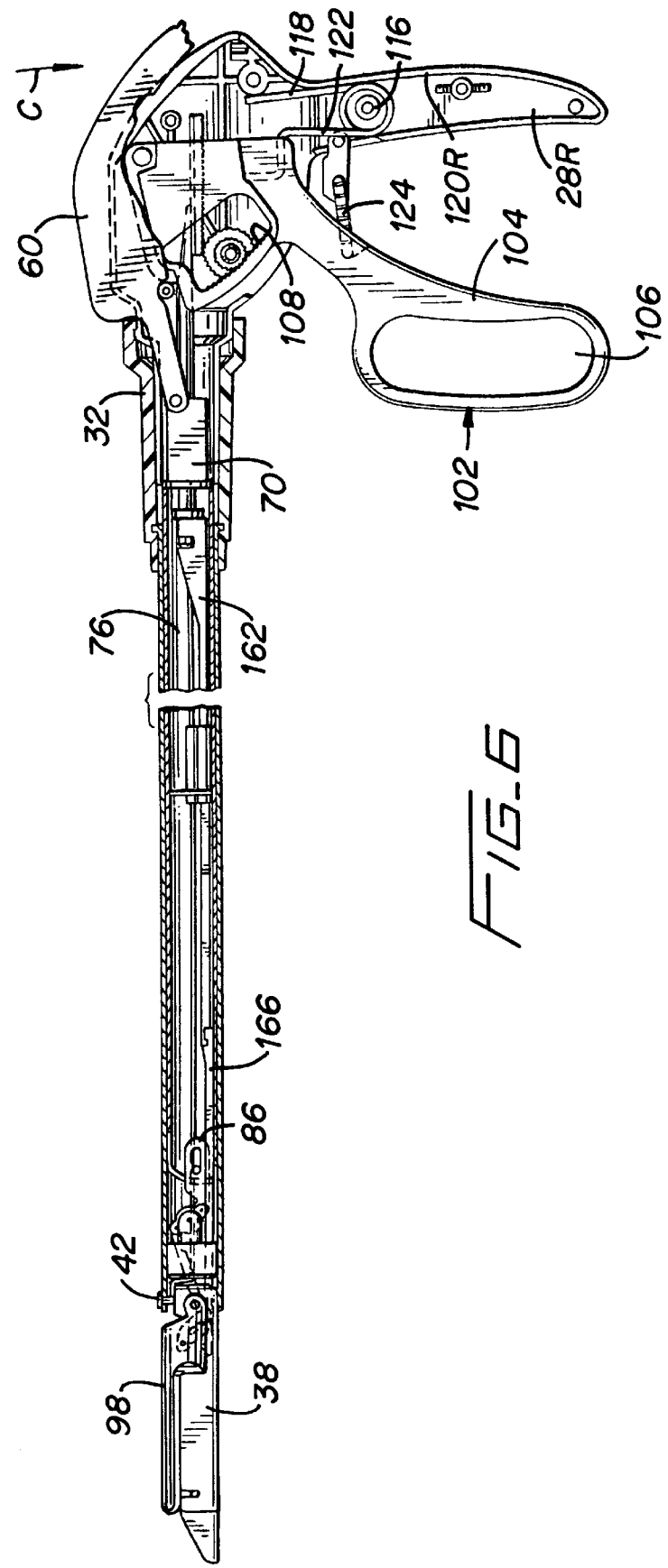
FIG. 6 is a side cross-sectional view, which illustrates the closing of the instrument's clamping mechanism.

Referring now to FIGS. 5, 5A and 6, the operation of the clamping feature of surgical stapler 20 will now be described in detail. Surgical instrument 20 is preferably initially oriented such that anvil 98 is in the clamped shut position as shown in FIG. 1. In this orientation, clamp approximation control lever 60 is oriented so that it is pivoted immediately adjacent handle body 28. When the user desires to open the clamp so as to position tissue between the fastener cartridge 118 and the anvil 98, clamp approximation lever 60 is lifted upwardly away from handle body 28 in the direction of Arrow "B" in FIG. 5. This motion causes proximal longitudinal motion of clamp pusher tube 72, which motion is translated by reverser link 92 into distal movement of flexible clamp links 94. Clamp cam 96 is, in turn, moved upwardly to open anvil 98. When it is desired to clamp anvil 98 in a closed position clamp approximation control lever 60 is simply pushed downwardly toward handle body 28, as indicated by Arrow "C" in FIG. 6, reversing the movements previously described.

With the tissue clamped between anvil 98 and fastener cartridge 118, the user, when prepared to fire the instrument, must first release safety 124 which is accomplished by simply pivoting safety 124 downwardly away from trigger 102 as shown in FIG. 7. Once safety 124 is released, the user then simply squeezes trigger 102 in the direction of Arrow "D" in FIG. 7, which drives rack rod 142 in a distal direction, thereby urging the interconnected firing channel member 162, flexible pushers 166, and camming sled 176 also in a distal direction to cam the fastener pushers 178 (FIG. 3) located in the fastener cartridge 118 and eject the staples therefrom.

Upon completion of firing the staples surgical stapler 20 may be reloaded with a new fastener cartridge as shown in FIG. 8 and reused again according to the above description.

Referring to FIGS. 9–12, another embodiment of the surgical stapler of the present disclosure designated as surgical stapler 200 will now be described in detail. As is apparent in FIG. 9, surgical stapler 200 is substantially the same both structurally and operationally as surgical stapler 20 as shown and described herein in connection with FIGS. 1–8. Accordingly, only those structural and operational details which differ from surgical stapler 20 will be addressed in detail herein.

Like surgical stapler 20, as noted above, surgical stapler 200 is configured to engage body tissue, apply a plurality of surgical fasteners thereto, and form an incision in the fastened body tissue during an endoscopic surgical procedure. In brief, surgical stapler 200 includes a handle portion 222, an elongate body portion 240 extending distally from handle portion 222, and a fastening and cutting portion 226 operatively associated with a distal end of body portion 224.

Figure 10:
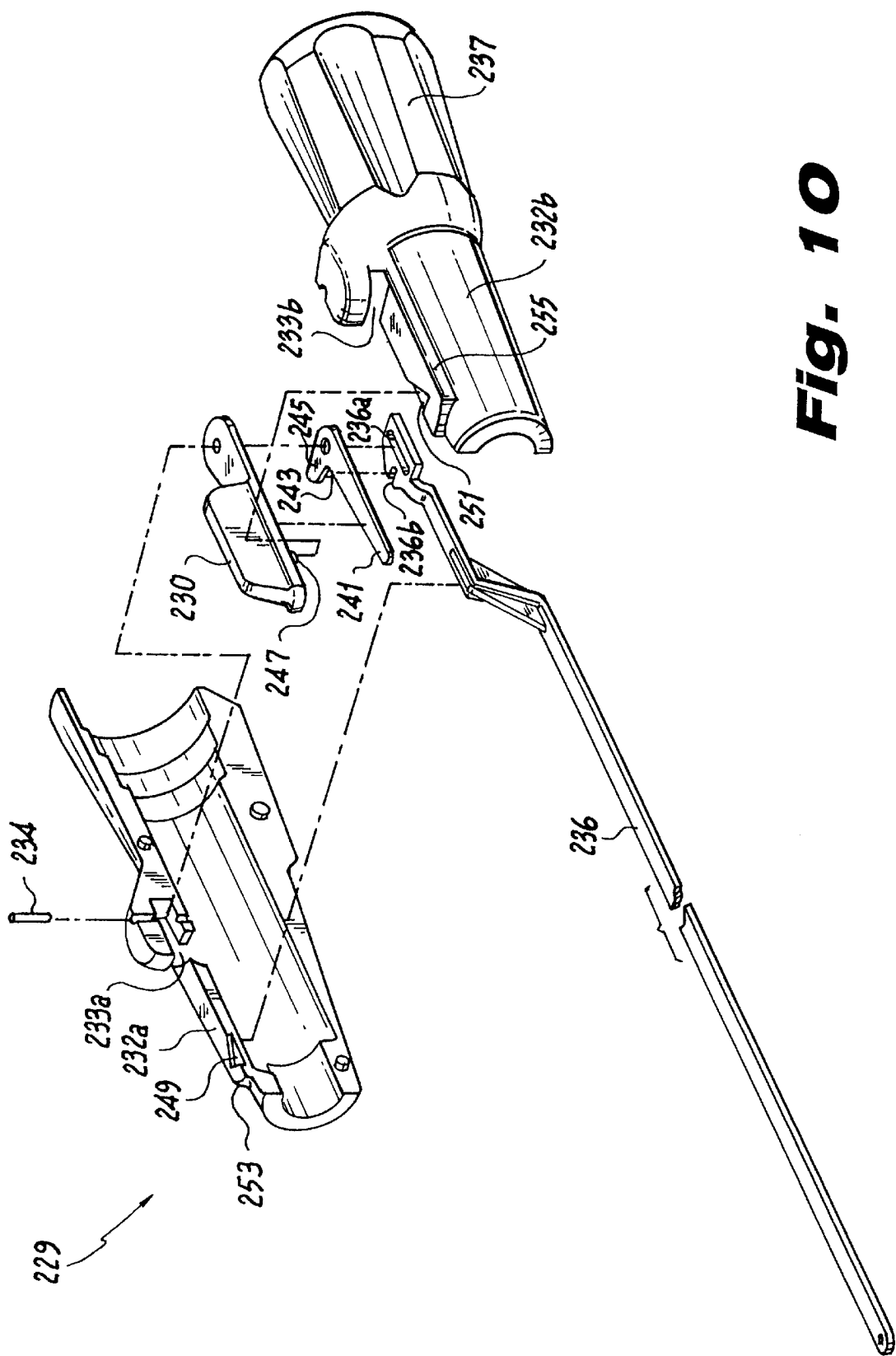
FIG. 10 is a perspective view, with parts separated, of the articulation actuation mechanism of the instrument of FIG. 9.

Referring to FIG. 10, surgical stapler 200 includes an articulation control mechanism 229 which effectuates bi-directional articulation of fastening and cutting portion 226. A rotation control handle 232 is provided as an abbreviated frustoconical structure having a central bore formed by the joining of arcuate split molded sections 232a and 232b. The split sections are preferably ultrasonically welded along the peripheral contacting surfaces thereof, although screws, adhesives, press fit structures or other suitable means of joining the two parts may also be utilized.

At a proximal end of rotation handle 232, knurling 237 may be provided to facilitate rotation of the body portion 224 and the fastening and cutting portion 226. In particular, because of the engaging structural relationship of the rotation handle 232 and cover tube 240, rotation of handle 232 effects rotation of cover tube 240, indicated by Arrow "F" in FIG. 9 and, therefore, rotation of the articulated fastening and cutting portion 226. Thus, positioning of surgical stapler 200 is facilitated without requiring the user to manipulate the entire instrument which may be difficult to accomplish during the procedure being performed.

Figure 9:
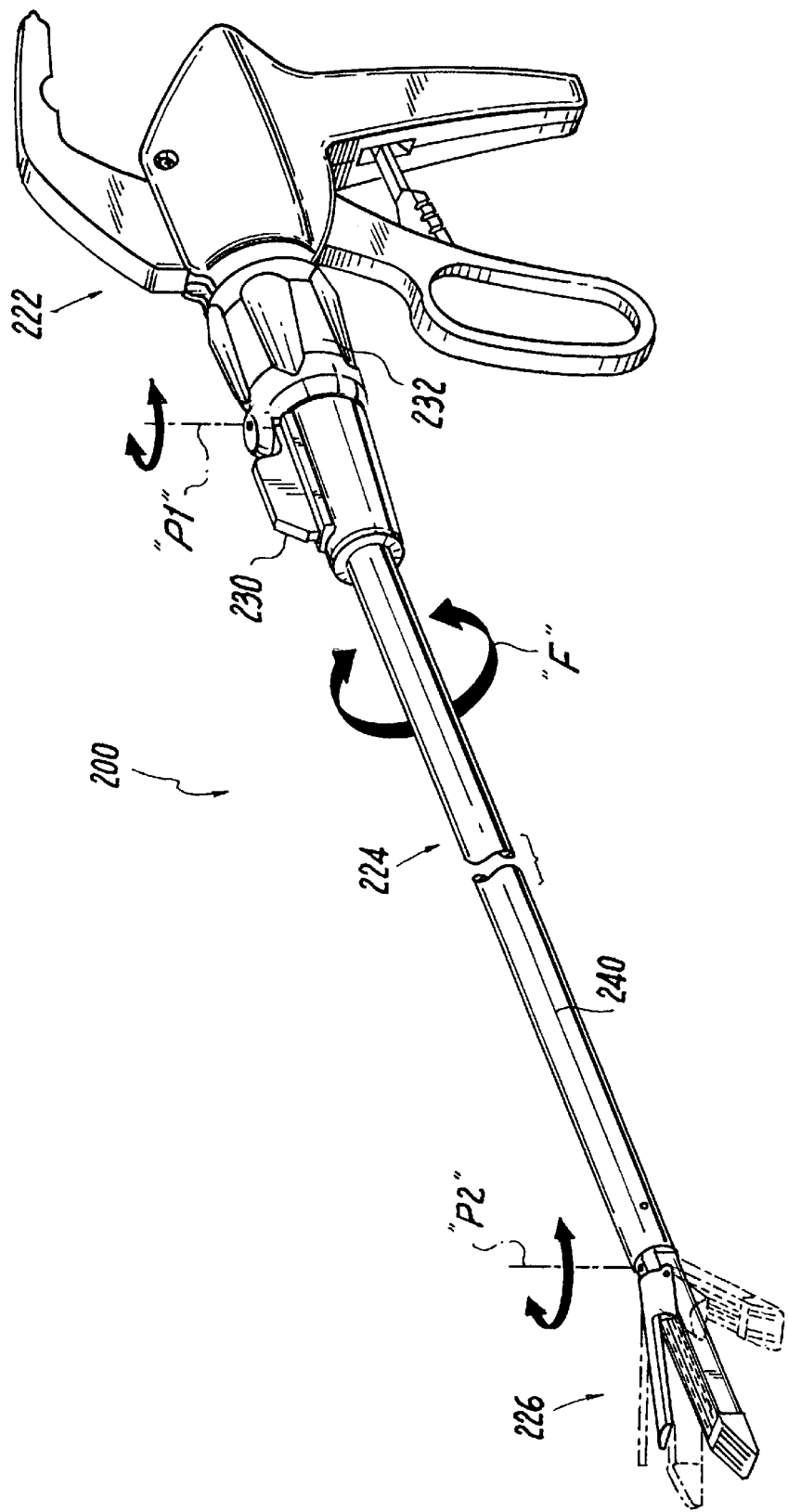
FIG. 9 is a perspective view of further embodiment of a surgical stapling instrument in accordance with the present disclosure.

Articulation control lever 230 is preferably a molded polycarbonate material and is pivotally mounted to rotation handle 232 in a clevis. The clevis is formed by clevis portions 233a and 233b which are preferably molded into rotation handle half-sections 232a and 232b, respectively such that articulation control lever 230 pivots about a pivot axis "P1" that passes longitudinally through pin 234, as shown in FIG. 9. Pivot axis "P1" preferably intersects the central longitudinal axis of the instrument 200 at a right angle.

An actuation control link rod 236 is provided which is preferably made of a rigid material such as stainless steel and has a longitudinal slot 236a spaced from but parallel to the central longitudinal axis of rod 236. Longitudinal slot 236a receives pin 234 to permit longitudinal translational movement of rod 236. A yoke 236b is formed near the proximal end of the rod 236. Yoke 236b defines an open ended slot which runs transverse relative to longitudinal slot 236a. At its distal end, rod 236 is pivotally connected to one side of fastening and cutting portion 226 offset from the central longitudinal axis of surgical stapler 200. Fastening and cutting portion 226 is pivotally connected to the distal end of cover tube 240 along the central longitudinal axis of surgical stapler 200 and defines pivot axis "P2".

A lever 241 is provided as part of the articulation control mechanism 229 and is preferably made of a rigid material such as stainless steel to transmit the forces created upon pivotal rotation of articulation control lever 230. Lever 241 is secured to articulation control lever 230 such that the two members rotate together as a unit. Lever 241 is provided with a fixed pin 243 formed on a transversely extending leg portion 245. Pin 243 is fitted in the slot defined by yoke 236b. Thus, upon rotation of lever 241, pin 243 is permitted to move along the slot defined by yoke 236b. This movement is necessary due to the transverse movement component of the arcuate path taken by pin 243 about pivot axis "P1" during rotation of lever 241. The longitudinal movement component of the arcuate path taken by pin 243 during rotation of lever 241 provides the longitudinal reciprocating driving force which acts upon rod 236 at yoke 236b.

When surgical stapler 200 is in an unarticulated condition, articulation control lever 230 is longitudinally aligned with the central longitudinal axis of stapler 200 and rod 236 is positioned such that pin 234 is positioned at the midpoint of longitudinal slot 236a. The length of longitudinal slot 236a is predetermined to permit articulation of fastening and cutting portion 226 up to approximately 35 degrees to either side of central longitudinal axis of surgical stapler 200.

Figure 11:
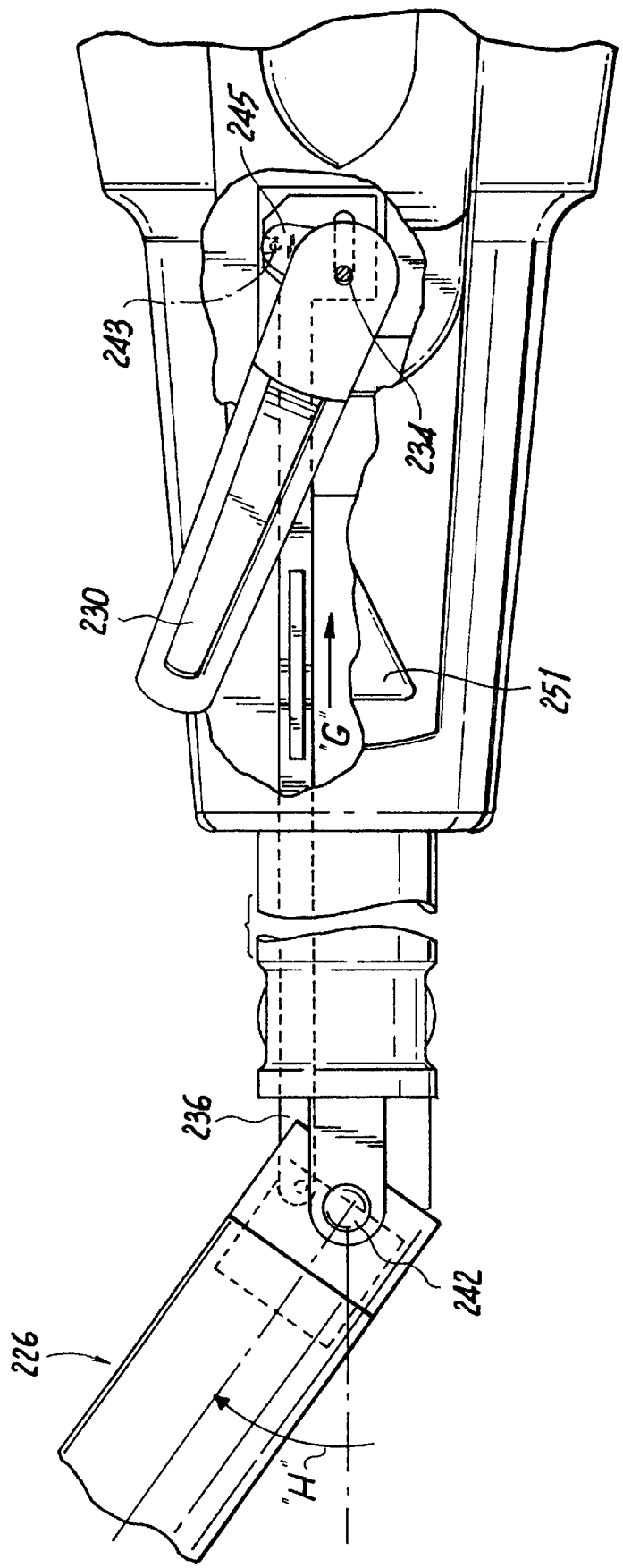
FIG. 11 is a top partially cut-away view which shows one operative position of the articulating mechanism of the instrument of FIG. 9.
Figure 12:
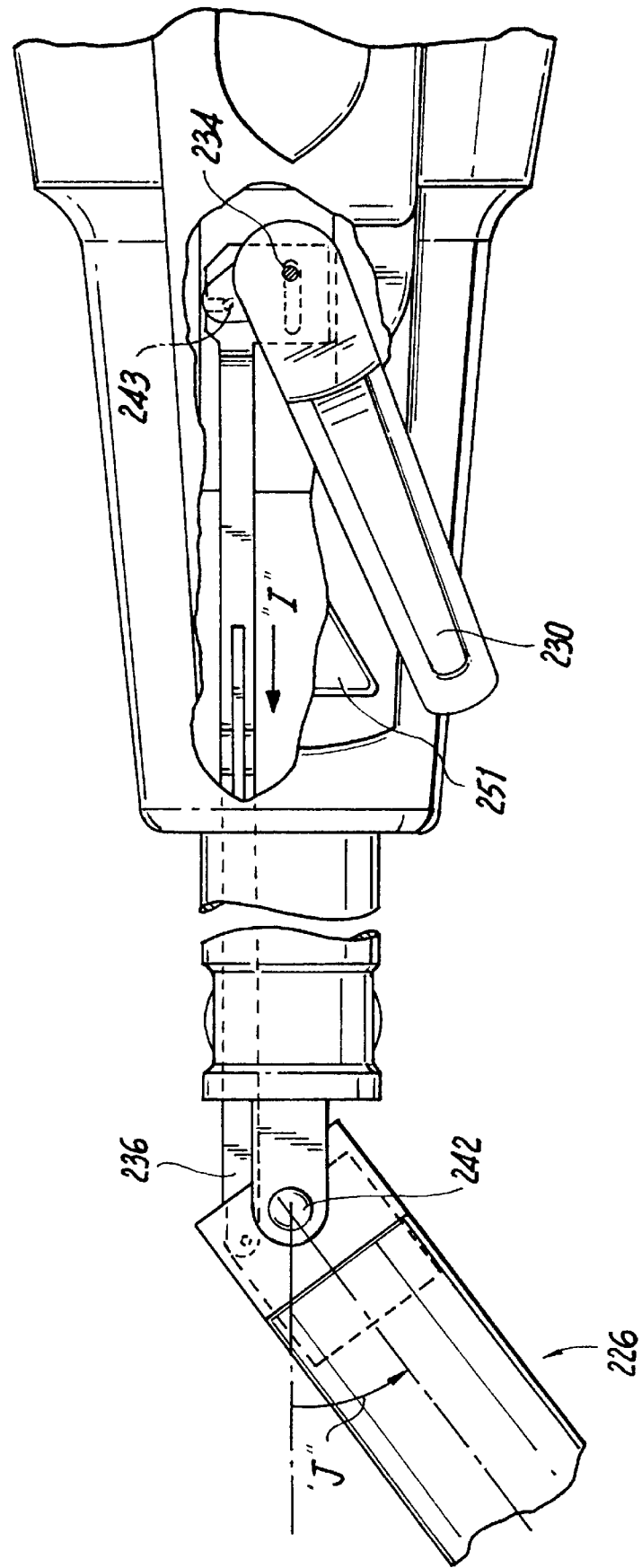
FIG. 12 is a top partially cut-away view, similar to FIG. 11, which shows another operative position of the articulating mechanism of the instrument of FIG. 9.

A further feature provided by the presently disclosed surgical stapler 200 is an articulation position maintaining arrangement which holds fastening and cutting portion 226 in one of three articulated positions, i.e., longitudinally aligned (FIG. 9), articulated to the right (FIG. 11), or articulated to the left (FIG. 12). Articulation control lever 230 is provided with a pair of raised knobs 247 which straddle lever 241. Rotation handle half-sections 232a and 232b are provided with right triangular shaped recesses 249 and 251 formed respectively therein. In this manner, when rotation handle half-sections are joined, recesses 249 and 251 form a triangle. Thus, when articulation control lever 230 is in the longitudinally aligned position (FIG. 9), knobs 247 are seated within the triangle defined by recesses 249 and 251. This inhibits movement of lever 230 and articulation of fastening and cutting portion 226 to either side.

Upon the application of torque to articulation control lever 230 to the right, as shown in FIG. 11, rod 236 will be urged proximally as indicated by arrow "G", thereby urging fastening and cutting portion 226 to articulate to the right as indicated by arrow "H". In this condition, knobs 247 are urged out of recess 249 to the outside of raised wall portion 253 molded as part of rotation handle half-section 232a. Articulation control lever 230 is maintained in this position until a sufficient torque is applied to the left in order to overcome the resistance supplied by knobs 247 against wall portion 253.

Articulation of fastening and cutting portion 226 to the left is the mirror image of the previously described articulation to the right. That is, upon the application of torque to articulation control lever 230 to the left, as shown in FIG. 12, rod 236 will be urged distally as indicated by arrow "I", thereby urging fastening and cutting portion 226 to articulate to the left as indicated by arrow "J". In this condition, knobs 247 are urged out of recess 251 to the outside of raised wall portion 255 molded as part of rotation handle half-section 232b. Articulation control lever 230 is maintained in this position until a sufficient torque is applied to the right in order to overcome the resistance supplied by knobs 247 against wall portion 255.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. Apparatus for applying surgical fasteners to body tissue, which comprises:
    a) a body having a proximal portion defining a central longitudinal axis and an articulating distal portion;
    b) a fastener cartridge containing at least one surgical fastener therein and positionable in the articulating distal portion;
    c) an anvil mounted adjacent the fastener cartridge and defining a fastener forming surface against which surgical fasteners are formed when ejected from the fastener cartridge;
    d) a fastener driving mechanism operatively associated with the fastener cartridge and actuable to eject the at least one fastener from the fastener cartridge;
    e) a single, substantially rigid link member having a distal portion offset from the body central longitudinal axis and pivotably connected to the articulating distal portion at a point spaced form the body central longitudinal axis, the link member being movable between a proximal-most position and a distal-most position to move the distal portion from an articulated condition away from the central longitudinal axis on a first side of the body to an articulated condition away from the central longitudinal axis on a second side of the body, the ink member being movable to a central position wherein the articulating distal portion is aligned with the central longitudinal axis of the proximal portion; and
    f) a control lever connected to the link member and pivotable about a point located along the body central longitudinal axis between a first position corresponding to the proximal-most position of the link member and a second position corresponding to the distal-most position of the link member.

2. Apparatus for applying surgical fasteners to body tissue according to claim 1, wherein the control lever defines a pivot point and includes an elongated portion extending from the pivot point, wherein when the control lever is positioned in the first position, the elongated portion is disposed to the first side of the body and when the control lever is positioned in the second position, the elongated portion is disposed to the second side of the body.

3. Apparatus for applying surgical fasteners to body tissue according to claim 1, wherein the articulating distal portion is moveable to an articulated condition up to 35 degrees from the central longitudinal axis.

4. Apparatus for applying surgical fasteners to body tissue, which comprises:
    a) a handle;
    b) an elongated body extending from the handle and defining a central longitudinal axis;
    c) a fastener cartridge housing pivotably connected to a distal end portion of the elongated body;
    d) a fastener cartridge containing a plurality of surgical fasteners and positionable in the cartridge housing;
    e) an anvil mounted adjacent the cartridge housing and defining a fastener forming surface against which surgical fasteners are driven when ejected from the fastener cartridge;

f) a fastener driving mechanism operatively associated with the fastener cartridge and actuatable from the handle to eject fasteners from the fastener cartridge;

g) a single, substantially rigid link member having a distal portion offset from the elongated body central longitudinal axis and pivotably connected to the cartridge housing, the link member being movable between a proximal-most position and a distal most position to move the cartridge housing from an articulated condition extending from a first side of the elongated body central longitudinal axis to an articulated condition extending from a second side of the elongated body central longitudinal axis the link member being movable to a central position wherein the cartridge housing is aligned with the central longitudinal axis; and h) a control lever connected to the handle and pivotable about a point located along the elongated body central longitudinal axis connected to the link and pivotable between a first position corresponding to the proximal-most position of the link member and a second position corresponding to the distal-most position of the link member.

5. Apparatus for applying surgical fasteners to body tissue according to claim 4, wherein the control lever defines a pivot point and includes an elongated portion extending from the pivot point, wherein when the control lever is positioned in the first position, the elongated portion is disposed to the first side of the elongated body and when the control lever is positioned in the second position, the elongated portion is disposed to the second side of the elongated body.

6. Apparatus for applying surgical fasteners to body tissue according to claim 4, wherein the fastener cartridge housing is moveable to an articulated condition up to 35 degrees from the central longitudinal axis.

7. Apparatus for applying surgical fasteners to body tissue according to claim 4, wherein the elongated body is rotatably connected to the handle.

* * * * *